United States Patent
Vodyanoy et al.

(10) Patent No.: US 8,273,381 B1
(45) Date of Patent: Sep. 25, 2012

(54) COMPOSITIONS FOR AND METHODS OF CONTROLLING OLFACTORY RESPONSES TO ODORANTS

(75) Inventors: Vitaly J. Vodyanoy, Auburn, AL (US); Lewis G. Scharpf, Jr., Auburn, AL (US); Alexandre Samoylov, Auburn, AL (US); Nilmini Viswaprakash, Auburn, AL (US); Ludmila Petrovna Globa, Auburn, AL (US); Edward E. Morrison, Auburn, AL (US)

(73) Assignee: Auburn University, Auburn, AL (US)

( * ) Notice: Subject to any disclaimer, the term of this patent is extended or adjusted under 35 U.S.C. 154(b) by 493 days.

(21) Appl. No.: 12/079,661

(22) Filed: Mar. 27, 2008

Related U.S. Application Data

(63) Continuation-in-part of application No. 11/786,898, filed on Apr. 13, 2007, now abandoned.

(60) Provisional application No. 60/920,439, filed on Mar. 28, 2007, provisional application No. 60/792,357, filed on Apr. 14, 2006.

(51) Int. Cl.
*A61K 33/30* (2006.01)
*A61K 8/27* (2006.01)
*A61P 27/00* (2006.01)

(52) U.S. Cl. ........................ 424/641; 424/489

(58) Field of Classification Search .................. None
See application file for complete search history.

(56) References Cited

U.S. PATENT DOCUMENTS

| | | | |
|---|---|---|---|
| 5,914,101 A | 6/1999 | Tapley et al. | 424/59 |
| 7,008,647 B2 | 3/2006 | Burrell et al. | |
| 7,078,023 B1 * | 7/2006 | McShane | 424/67 |
| 7,087,249 B2 | 8/2006 | Burrell et al. | |
| 2004/0110738 A1 | 6/2004 | Gillis et al. | |
| 2004/0241423 A1 | 12/2004 | Ramin et al. | 428/323 |
| 2005/0065102 A1 | 3/2005 | Tohyama et al. | 514/44 |
| 2007/0020201 A1 * | 1/2007 | Boyd et al. | 424/52 |

OTHER PUBLICATIONS

Turin, L. A Spectroscopic Mechanism for Primary Olfactory Reception. Chem. Senses 21: 773-791 (1996).*

Lok et al., "Proteomic Analysis of the Mode of Antibacterial Action of Silver Nanoparticles," Journal of Proteome Research, 2006, vol. 5, pp. 916-924.

* cited by examiner

*Primary Examiner* — David J Blanchard
*Assistant Examiner* — Peter Anthopolos
(74) *Attorney, Agent, or Firm* — Haverstock & Owens LLP

(57) ABSTRACT

A composition, system and method for modifying an olfactory response to an odorant is disclosed. In some embodiments, the composition includes crystalline metal nanoparticles dispersed in an aqueous medium. The composition is applied to olfactory tissues using a suitable applicator or dispenser. The metal nanoparticles are believed to interact with a G-protein coupled to receptor located in the cilia to moderate (enhance or reduce) sensitivity or ability to smell particular odorants. In accordance with an embodiment of the invention, the composition includes one or more odorants.

22 Claims, 12 Drawing Sheets

COMPOSITIONS FOR AND METHODS OF CONTROLLING OLFACTORY RESPONSES TO ODORANTS

RELATED APPLICATIONS

This application is a continuation-in-part of U.S. patent application Ser. No. 11/786,898, filed on Apr. 13, 2007 now abandoned and entitled COMPOSITIONS FOR AND METHODS OF CONTROLLING OLFACTORY RESPONSES TO ODORANTS" which is hereby incorporated by reference, and which claims priority under 35 U.S.C. §119(e) of U.S. Provisional Patent Application Ser. No. 60/792,357, filed on Apr. 14, 2006, and titled "COMPOSITIONS AND METHODS FOR ENHANCING OLFACTORY RESPONSE TO ODORANTS," the contents of which are hereby incorporated by reference.

This application also claims priority under 35 U.S.C. §119 (e) from the U.S. Provisional Patent Application Ser. No. 60/920,439, filed on Mar. 28, 2007, and titled "METHOD OF ODORANT INDUCED RESPONSE BY COMBINATION OF METAL PARTICLES AND OLFACTORY SENSORY NEURONS," the contents of which are hereby incorporated by reference.

FIELD OF THE INVENTION

This invention relates generally to compositions and methods of modulating or controlling olfactory responses to an odorant. More specifically, this invention relates to metal compositions and methods for modulating or controlling olfactory responses to an odorant.

BACKGROUND OF THE INVENTION

In the human world, olfaction serves to heighten or discriminate our aesthetic sense, while in other animals it is an important survival sense, upon which the well-being and sometimes the safety of the animal itself is dependent on. The partial or complete loss of smell (anosmia) affects approximately 2.5 million people in the United States and poses serious health risks as the presence of rancid food; toxic odors and smoke often go undetected. The clinical treatment of anosmia will require a better understanding of the mechanisms that regulate differentiation, proliferation and the injury response of the precursor, the multi-potent neuronal stem cells in the olfactory epithelium (OE). Olfactory receptor neurons (ORN) are the only mamalian neurons which undergo continuous neurogenesis through their life, suggesting that a neuronal stem cell exists in this system.

An aroma compound, also known as odorant, aroma, fragrance, flavor, is a chemical compound that has a smell or odor. A chemical compound has a smell or odor when two conditions are met: the compound needs to be volatile, so it can be transported to the olfactory system in the upper part of the nose, and it needs to be in a sufficiently high concentration to be able to interact with one or more of the olfactory receptors. Typically, odorants are small molecules in a range of 40 to 400 Daltons.

Aroma compounds can be found in food, wine, spices, perfumes, fragrance oils, and essential oils. For example, many aroma compounds form biochemically during ripening of fruits and other crops. In wines, most form as byproducts of fermentation. Odorants can also be added to a dangerous odorless substance, like natural gas, as a warning. Many of the aroma compounds also play a significant role in the production of flavorants, which are used in the food service industry to flavor, improve and increase the appeal of their products.

The olfactory mucosa is an organ made up of the olfactory epithelium and mucus. The mucus protects the olfactory epithelium and allows odors to dissolve so that they can be detected by olfactory receptor neurons. In mammals, the olfactory mucosa is located on the roof of the nasal cavity, above and behind the nostrils.

Cells in the olfactory mucosa have been shown to have a degree of plasticity. Because of this, these cells hold potential for therapeutic applications, have been used in clinical trials for adult stem cell therapeutic treatments, and have been successfully harvested for future applications.

The olfactory epithelium is a specialized epithelial tissue inside the nasal cavity that is involved in smell. In humans, the olfactory epithelium measures about 1 inch wide by 2 inches long (about 2 cm by 5 cm) and lies on the roof of the nasal cavity about 3 inches (about 7 cm) above and behind the nostrils. The olfactory epithelium is the part of the olfactory system directly responsible for detecting odors.

The tissue is made of three types of cells: the olfactory receptor neurons, which transduce the odor to electrical signals, the supporting cells, which protect the neurons and secrete mucus, and the basal cells, which are a type of stem cell that divide into olfactory receptor neurons to replace dead receptor neurons. The olfactory epithelium is divided into four zones from ventral to dorsal. Each olfactory receptor is expressed throughout one zone.

In mammals, odorants are inhaled through the nose where they contact the olfactory epithelium. Olfactory receptor neurons in the olfactory epithelium transduce molecular features of the odorants into electrical signals which then travel along the olfactory nerve into the olfactory bulb. Axons from the olfactory sensory neurons converge in the olfactory bulb to form tangles called glomeruli (singular glomerulus). Inside the glomulerus, the axons contact the dendrites of mitral cells and several other types of cells. Mitral cells send their axons to a number of brain areas, including the piriform cortex, the medial amygdala, and the entorhinal cortex. The piriform cortex is probably the area most closely associated with identifying the odor. The medial amygdala is involved in social functions such as mating and the recognition of animals of the same species. The entorhinal cortex is associated with memory. The exact functions of these higher areas are a matter of scientific research and debate.

Olfactory receptors belong to class A of the G protein-coupled receptor. In vertebrates, the olfactory receptors are located in the cilia of the olfactory sensory neurons. In insects, olfactory receptors are located on the antennae. Sperm cells also express odor receptors, which are thought to be involved in chemotaxis to find the egg cell.

It is believed that rather than binding to specific ligands like most receptors, olfactory receptors bind to structures on odor molecules. Once the odorant has bound to the odor receptor, the receptor undergoes structural changes and it binds and activates the olfactory-type G protein on the inside of the olfactory receptor neuron. The G protein (Golf and/or Gs) in turn activates the lyase adenylate cyclase, which converts ATP into cyclic AMP (cAMP). The cAMP opens ion channels that allow calcium and sodium ions to enter into the cell, depolarizing the olfactory receptor neuron and beginning an action potential which carries the information to the brain.

There are a wide range of different odor receptors, with as many as 1,000 in the mammalian genome. Olfactory receptors may make up as much as 3% of the genome. Only a portion of these potential genes form functional odor receptors. According to an analysis of the Human genome project, humans have 347 functional genes coded for olfactory receptors. The reason for the large number of different odor receptors is to provide a system for detecting as many different odors as possible. Even so, each odor receptor does not correspond to just one odor. Each individual odor receptor is broadly tuned to be activated by a number of similar structures. Like the immune system, this system allows molecules that have never been encountered before to be characterized. Also, most odors activate more than one type of odor receptor. This aspect provides for the identification of an almost limitless number of different molecules.

Damage to the olfactory system can occur for a number of different reasons. For example, damage to the olfactory system can occur by traumatic brain injury, cancer, inhalation of toxic fumes, or neurodegenerative diseases such as Parkinson's disease and Alzheimer's disease. These conditions can cause anosmia (complete loss of ability to detect odors) or hyposmia (partial loss of the ability to detect odors). Even old age can cause anosmia or hyposmia; in fact most people suffer from some degree of hyposmia with aging.

The ability to smell is important not only to the survival of human beings, but is also an important aspect of a fulfilling life experience. The loss of smell can have a far reaching impact on a person's metal health and overall quality of life. Therefore, there is a continued need to develop techniques for maintaining, enhancing or improving the ability to smell odorants, especially for those people who exhibit anosmia. There is also a need to develop techniques for reducing the ability to smell an odorant or odorants, especially when the odorant or odorants are non-toxic but still unpleasant.

SUMMARY OF THE INVENTION

The present invention is directed to compositions, systems and methods for modifying an olfactory response to one or more odorants. In accordance with the embodiments of the invention, a composition (also referred to herein as a metal composition) includes metal in the form of metal clusters, metal compounds, metal particles or a combination thereof. The metal, when applied to the olfactory tissue, associates with or binds with G-protein coupled to receptors located in the cilia. This association or binding modulates the cascade of events that ultimately leads to the sensation of smell.

The metal, in accordance with an embodiment of the invention, is in the form of metal nanoparticles. The metal nanoparticles are able to include any metal element or combination of metal elements including, but not limited to, Ag, Pd, Rh, Cu, Pt, Ni, Fe, Ru, Os, Mn, Cr, Mo, Au, W, Co, Ir, Zn and Cd metal elements. In some embodiments, the metal nanoparticles are crystalline metal nanoparticles having a molar concentration in the composition that is in the range of $10^{-15}$ to $10^{-9}$ Moles.

In accordance with the embodiments of the invention the composition also includes a delivery medium. The delivery medium is able to be a liquid, a powder, an emulsion, a suspension, a vapor or any suitable delivery medium for holding, storing and applying the metal to an olfactory tissue, such as an olfactory mucosa membrane. In some embodiments, the delivery medium is substantially liquid or vapor. The delivery medium is also able to include stabilizers, preservatives and/or surfactants to provide a formulation that is suitable for application to the olfactory tissue. For example, the delivery medium is able to include one or more of a fatty acid, an amino acid, an ester, an ether, a polyether, an amine and a carboxylic acid.

The delivery medium is also able to include a biological component, which helps the metal interact with the olfactory tissue. For example, the delivery medium is able to include an olfactory binding protein.

In accordance with yet further embodiments of the invention, the composition includes one or more odorants. Suitable odorants include any number of synthetic or natural odorants. Suitable odorants include, but are not limited to, aromatics, ketones, alcohols, aldehydes, esters, amines, thiols, terpenes, essential oils and combinations thereof.

A system in accordance with the embodiments of the invention includes a delivery means, such as packaging or a dispenser for dispensing, applying or administering the composition, such as described above, to the olfactory tissue. The composition is able to be dispensed, applied or administered in the form of an aerosol spray, an aerated spray, liquid droplets, vapor or a plume of powder. Accordingly, suitable delivery means, packaging or dispensers include pressurized spray containers, a pump or squeeze spray container, dropper-bottle containers and powder adapted inhalers.

In accordance with the method of the invention, a metal composition, such as described above, is formed and packaged or stored. As described above the metal composition is able to include one or more stabilizers, preservatives, surfactants or odorants. Where the metal composition is a medicating composition, the composition is packaged with a suitable applicator or dispenser, such that the metal composition is able to be applied to olfactory tissues through a nasal passage. The composition of the present invention is able to be used to enhance or suppress sensitivity of olfactory senses to fragrances and other odorants.

In accordance with further methods of the invention a metal composition, such as described above, is applied to a surface of an object which contains an odorant. For example, a metal composition of the present invention can be sprayed on flowers to enhance the peoples sensitivity to the flower odorant or odorants.

DETAILED DESCRIPTION OF THE INVENTION

Figure 1A:
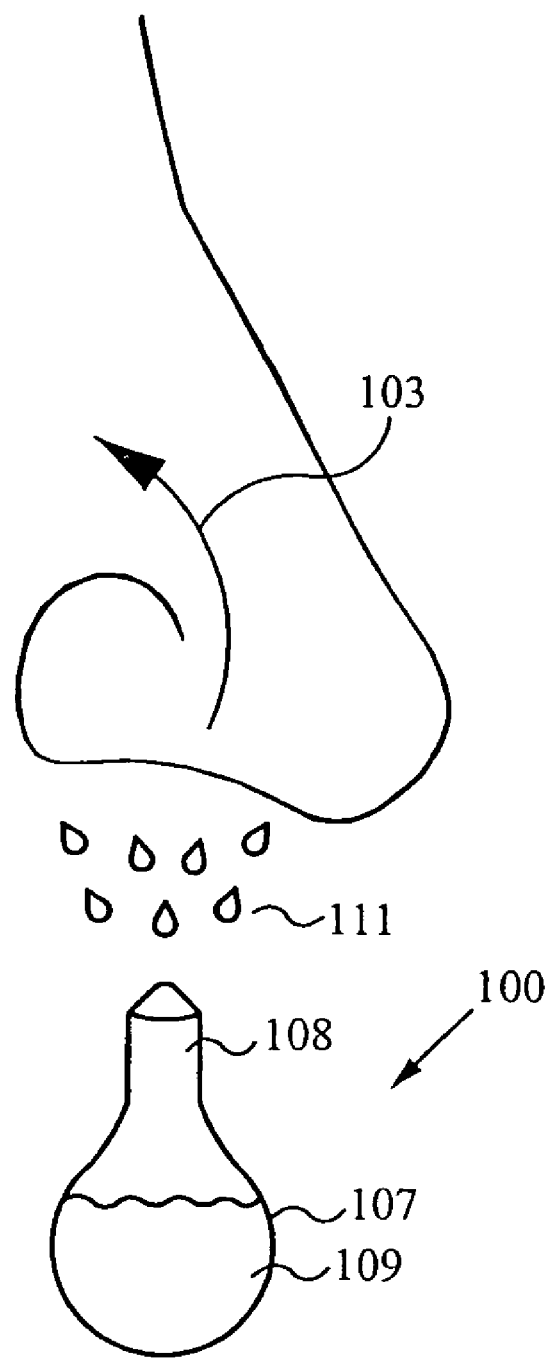
FIGS. 1A-C illustrate dispensers, packages and applicators for administering a composition to olfactory tissues, in accordance with the embodiments of the invention.

The process of how the binding of the ligand (odor molecule or odorant) to the receptor leads to an action potential in the receptor neuron is via a second messenger pathway depending on the organism. In mammals the odorants stimulate adenylate cyclase to synthesize cAMP via a G protein referred to as Golf. cAMP, which is the second messenger here, opens a cyclic nucleotide-gated ion channel (CNG) producing an influx of cations (largely $Ca^{+2}$ with some $Na_+$) into the cell, slightly depolarising it. The $Ca^{+2}$ in turn opens a $Ca^{+2}$ activated chloride channel leading to efflux of further depolarising the cell and triggering an action potential. $Ca^{+2}$ is then extruded through a sodium-calcium exchanger. A calcium-calmodulin complex also acts to inhibit the binding of cAMP to the cAMP dependent channel, thus contributing to olfactory adaptation. In this mechanism the cAMP works by directly binding to the ion channel rather than through activation of protein kinase A. It is similar to the transduction mechanism for photoreceptors in which the second messenger cGMP works by directly binding to ion channels, suggesting that maybe one of these receptors was evolutionarily adapted into the other. There are also considerable similarities in the immediate processing of stimuli by lateral inhibition.

The averaged activity of the receptor neuron to an odor can be measured by an electroolfactogram (EOG). In this process, fragments of olfactory epithelaia, either cultured or dissected from natural sources (e.g., mice and dogs), are placed in an EOG recording chamber with a buffer solution. The epithelial cilia are exposed. Electrodes are connected to the tissues through a patch-clamp amplifier to detect electrical activity of the olfactory epithelia. In general air puff or plums of an odorant mixture are applied over the olfactory epithelia through a small pipet or capillary, before and after being treated with the metal composition, described in detail below. The amplitude of the electrical signal to the amount of the odorant is plotted over time after the electrical signal is amplified and filtered.

A composition in accordance with the embodiments of the invention includes metal. The metal is able to be in the form of metal clusters, metal compounds, metal particles or a combination thereof. In accordance with an embodiment of the invention, the metal is in the form of metal nanoparticles (metal particles having an average diameter of 200 nanometers or smaller). The metal nanoparticles are able to include any metal element or combination of metal elements including, but not limited to, Ag, Pd, Rh, Cu, Pt, Ni, Fe, Ru, Os, Mn, Cr, Mo, Au, W, Co, Ir, Zn and Cd metal elements. In some embodiments, the metal nanoparticles are crystalline metal nanoparticles having a composition molar concentration in the composition that is in the range of $10^{-5}$ to $10^{-9}$ Moles.

In accordance with one embodiment of the invention, the metal nanoparticles come from a protein nucleating center (PNC) material, such as the PNC material that is able to be extracted from shark blood. PNC material typically comprises 20 to 400 metal atoms. Alternatively, the metal nanoparticles are produced using any number of techniques known in the art.

A composition also includes a delivery medium, in some embodiments. The delivery medium is able to be a liquid delivery medium such as water, alcohol, an emulsion, suspension, vapor or a combination thereof. The delivery medium is also able to be in the form of a powder. The composition can include any materials necessary to provide a formulation suitable for application or delivery of the composition to olfactory tissue or a surface. For example, the delivery medium is able to include one or more of a fatty acid, an amino acid, an ester, an ether, a polyether, an amine and a carboxylic acid. The delivery medium is also able to include a biological component, which can help the metal component of the composition interact with the olfactory tissue being treated. In some embodiments, any additives used in the formulation of the composition do not adversely effect the odorant that is being targeted.

In accordance with a particular embodiment of the invention, the composition includes one or more odorants. Suitable odorants include any number of synthetic or natural odorants including, but not limited to, aromatics, ketones, alcohols, aldehydes, esters, amines, thiols, terpenes, essential oils and combinations thereof.

Referring to FIG. 1A, a system 100 in accordance with the embodiments of the invention includes a delivery means or a dispenser for dispensing, applying or administering a composition 109, such as described above, to an olfactory tissue through a nasal passage 103. The delivery means or dispenser is able to be, for example, a bottle 107 with a spray nozzle 108 that produces an aerated spray 111 when the bottle 107 is squeezed.

Figure 1B:
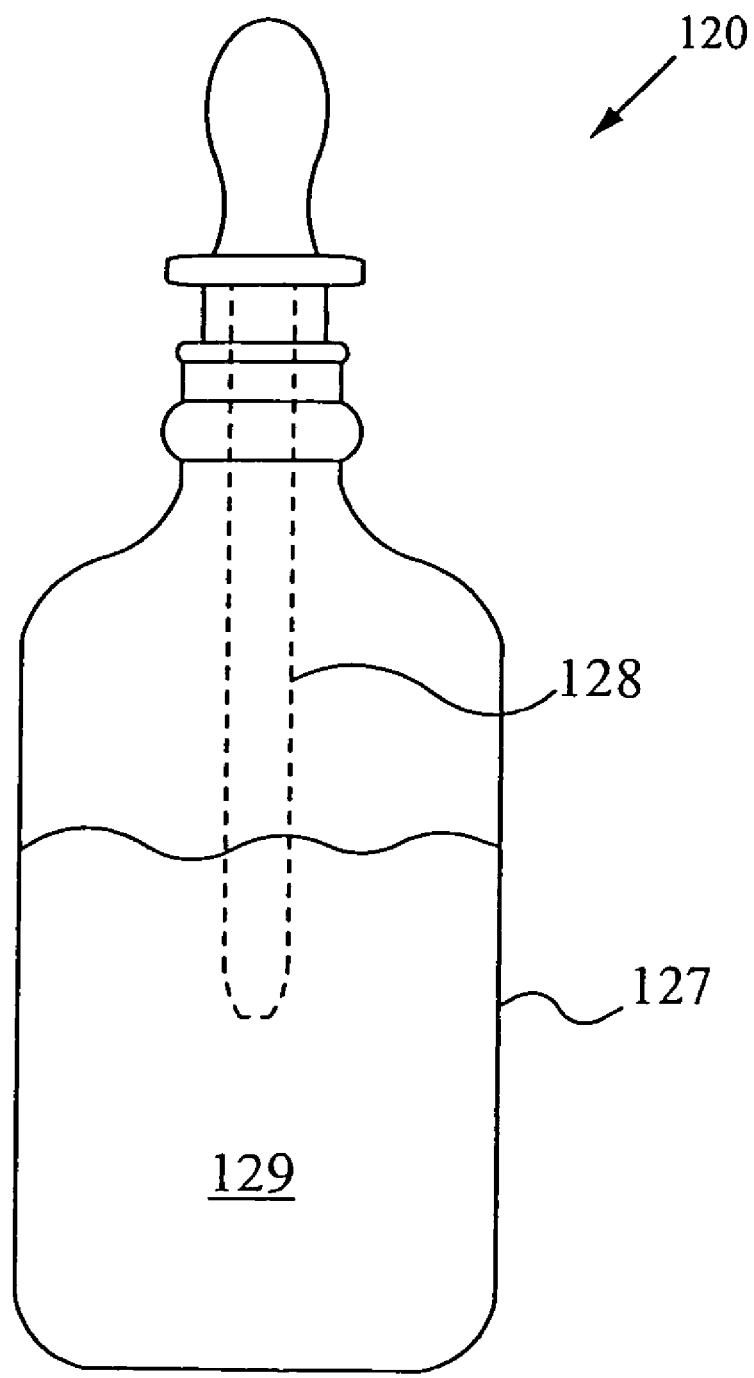

Referring to FIG. 1B, in an alternative embodiment of the invention, a system 120 includes a dropper-bottle dispenser 127 with a dropper 128 for dispensing, applying or administering a composition 129, such as described above, to an olfactory tissue through a nasal passage 103 (FIG. 1A) eyes and/or mouth (not shown).

Figure 1C:
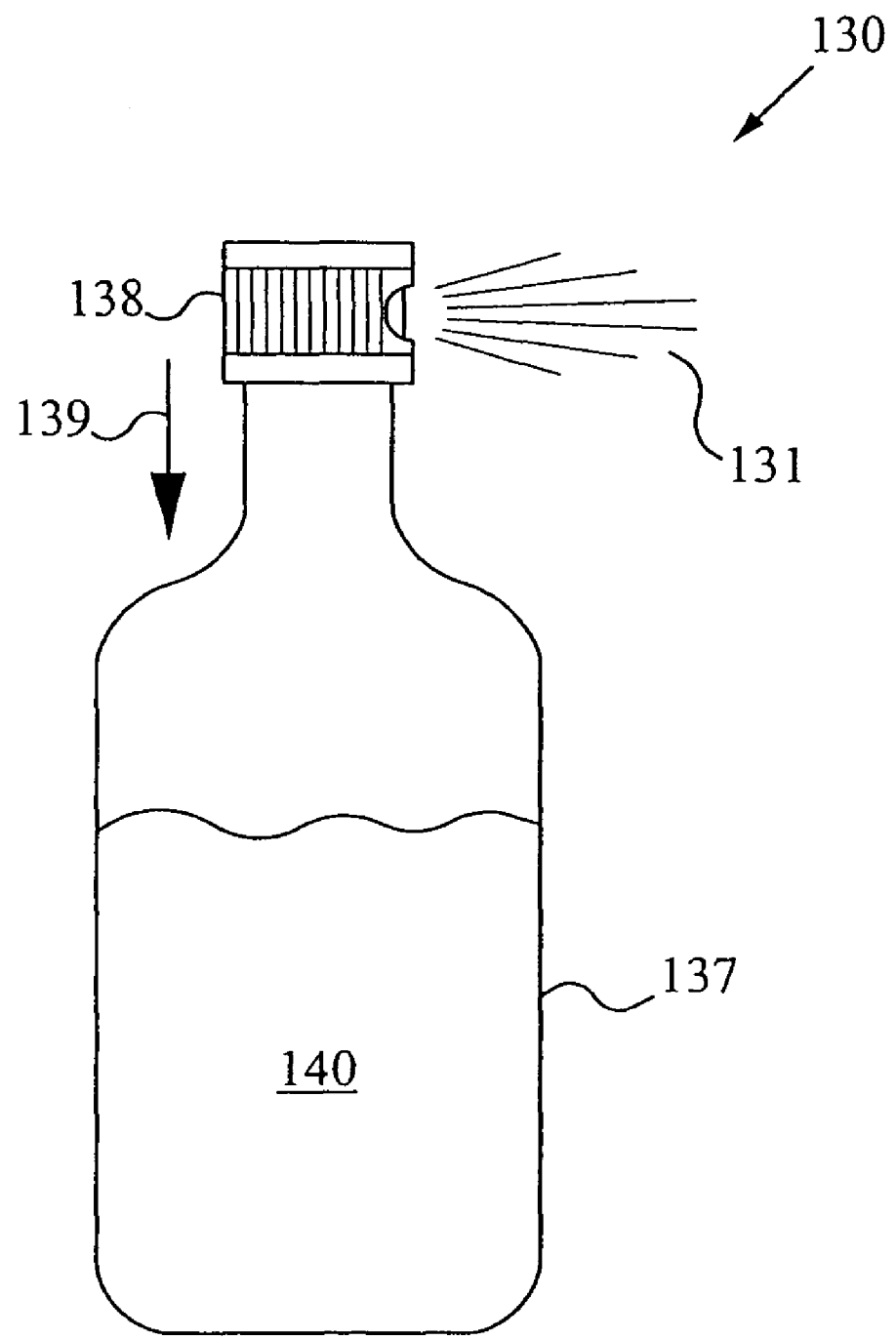

Referring to FIG. 1C, in an alternative embodiment of the invention, a system 130 includes a pump spray bottle dispenser 137 for dispensing, applying or administering a composition 140, such as described above. The pump spray bottle dispenser 137 provides a mist or a plume 131 that permeates the surrounding air when a pump mechanism 138 is pushed down, as indicated by the arrow 139. A portion of the mist or plume 131 is inhaled through a nasal passage 103 (FIG. 1A) and/or mouth or other mucus membranes and treats the olfactory tissue.

It will be clear to one skilled in the art from the discussions above and below that the composition of the present invention is able to be dispensed, applied or administered from any number of different delivery means or dispensers and the particular choice will depend on the physical properties of the composition and the intended application. The composition is able to, for example, be dispensed, applied or administered as an aerosol spray from a pressurized container or as a plume of powder from an inhaler. Regardless of how the composition is dispensed, applied or administered, the composition either directly contacts or treats an olfactory tissue or tissues and modifies sensitivity to a smell of one or more odorants. Alternatively, the composition is dispensed, applied or administered to a surface that includes an odorant and contacts the olfactory tissue or tissues through the air to modify the sensitivity to the smell of the one or more odorants.

Figure 2A:
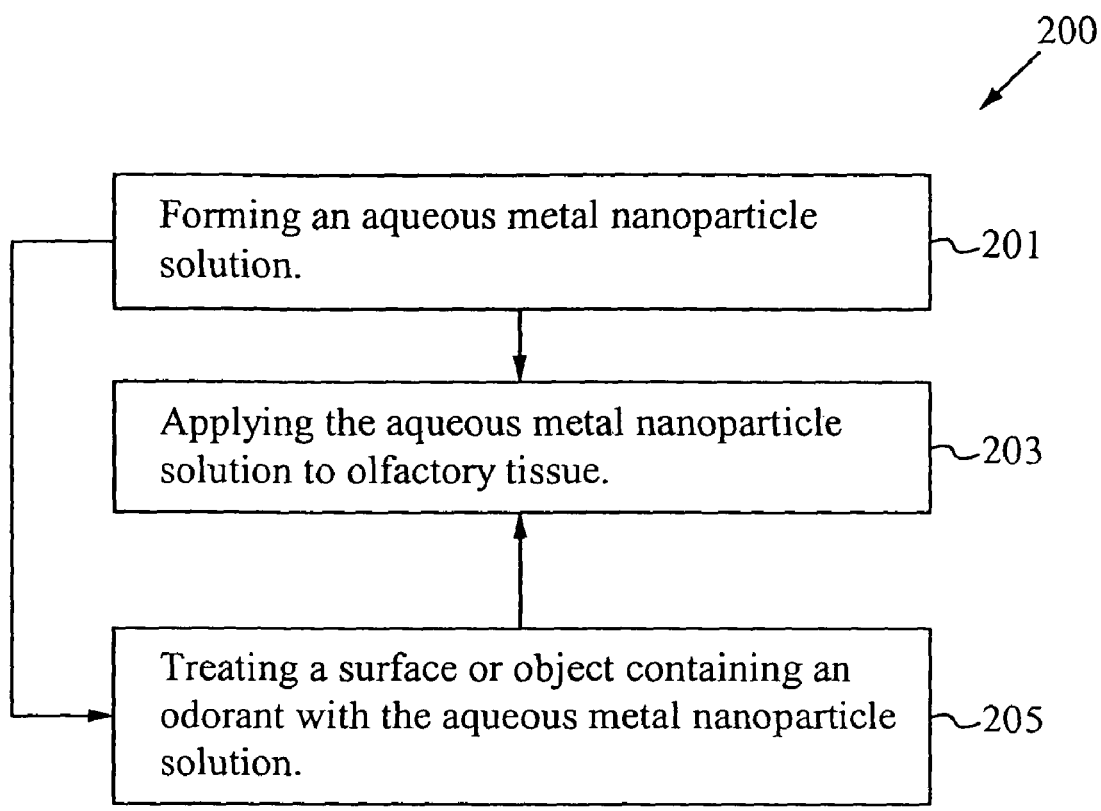
FIGS. 2A-B are block flow diagrams outlining steps for modulating sensitivity to the ordorant, in accordance with the embodiments of the invention.

FIG. 2A is block flow diagram 200 outlining steps, in accordance with a method of the present invention. In the step 201 an aqueous metal nanoparticle solution, as also referred to above as a composition, is formed. The aqueous metal nanoparticle solution is formed in the step 201 by isolating metal nanoparticles from a natural source (a PNC material), from a synthetic material, or from both. The aqueous metal nanoparticle solution is able to be formed with or mixed with emulsions, solvents, stabilizers, ligands, preservatives, surfactants, odorants, biological materials, or any other material or materials to form an aqueous metal nanoparticle solution suitable for the application at hand. After the aqueous metal nanoparticle solution is formed in the step 201, in the step 203 the metal nanoparticle solution is dispensed, applied or administered to olfactory tissues using any number of different ways, such as described above with reference to FIGS. 1A-C. For example, in the step 203 the metal nanoparticle solution is dispensed, applied or administered directly to olfactory tissues using a dispenser. Alternatively, prior to the step 203, a surface or an object containing an odorant is treated with the metal nanoparticle solution in the step 205. Accordingly, the metal nanoparticle solution is then dispensed, applied or administered indirectly to olfactory tissues through the air.

Figure 2B:
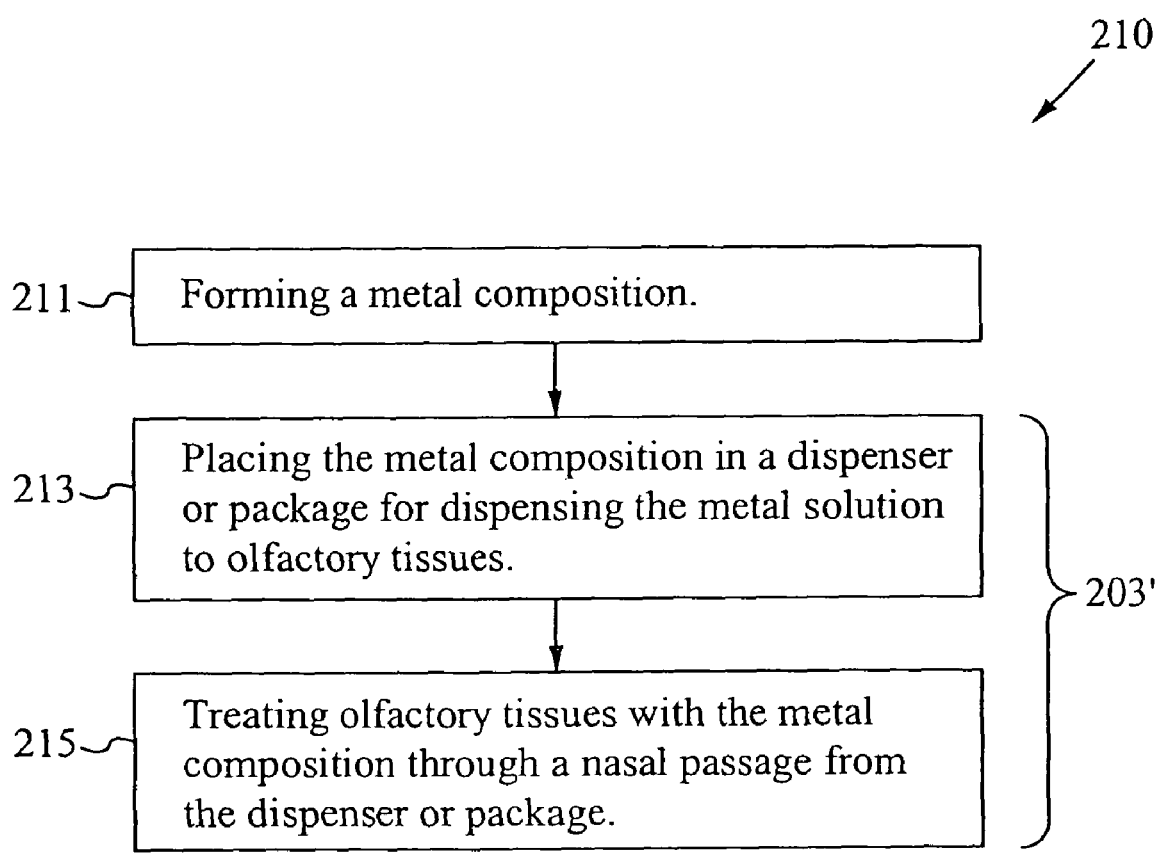

FIG. 2B shows a block flow diagram 210 outlining steps in accordance with a further embodiment of the invention. In the step 211 a metal composition is formed that includes metal clusters, metal compounds, metal particles or a combination thereof is formed. The metal composition also includes a suitable binder material and/or solvent. The metal composition is also able to include emulsions, stabilizers, ligands, preservatives, surfactants, odorants, biological materials, or any other material or materials to form a metal composition suitable for the application at hand. After the metal composition is formed in the step 211, in the steps 203' the metal composition is dispensed, applied or administered to an olfactory tissue, the source or surface of an object, using any number of different ways, such as described above with reference to FIGS. 1A-C. The steps 203' include placing the metal composition in a dispenser or package in the step 213 and treating olfactory tissues with the metal composition through a nasal passage 103 (FIG. 1A) from the dispenser or package in the step 215.

Figure 3A:
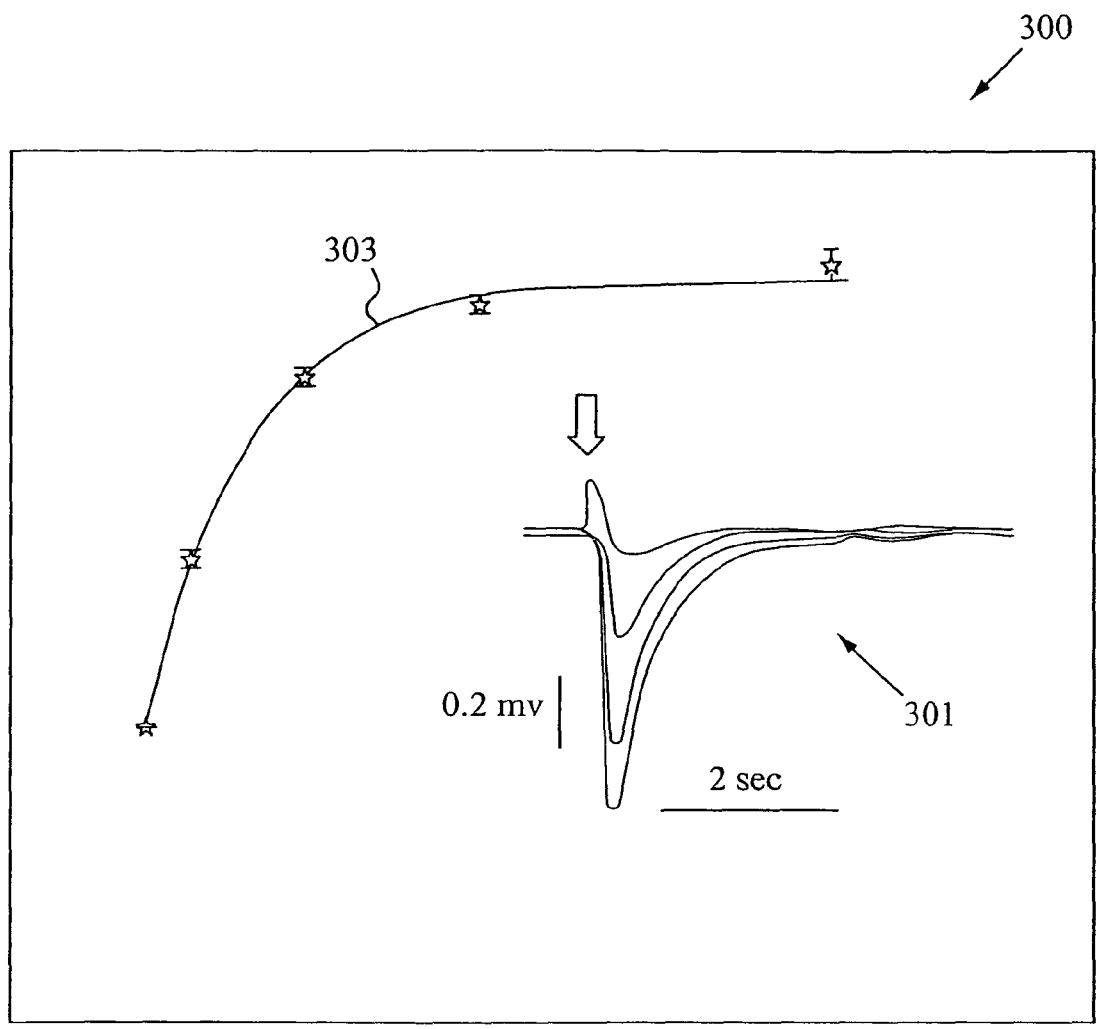
FIG. 3A is a graph of Electroolfactogram recordings of an olfactory tissue exposed to protein nucleation center material and an odorant, in accordance with the embodiments of the invention.

FIG. 3A is a graph 300 showing amplitude plots 301 of Electroolfactogram recordings. The amplitude plots 301 show the electrical responses of an olfactory tissue treated with a composition that contains a protein nucleation center material and that is exposed to an odorant. As described above, the olfactory tissue is placed in an EOG recording chamber with a buffer solution and connected to electrodes through an amplifier. Air puffs or plumes of an odorant mixture are applied over the olfactory tissue and the electrical response is measured and plotted. The line 303 plot normalized peak amplitudes over time. In some cases a ten-fold increase in the electrical response of the olfactory tissue to an odorant has been observed using the method of the present invention. This ten-fold increase in the electrical response of the olfactory tissue is believed to substantially correlate with a ten-fold increase in sensitivity to the odorant and/or enhancement of smell.

Figure 3B:
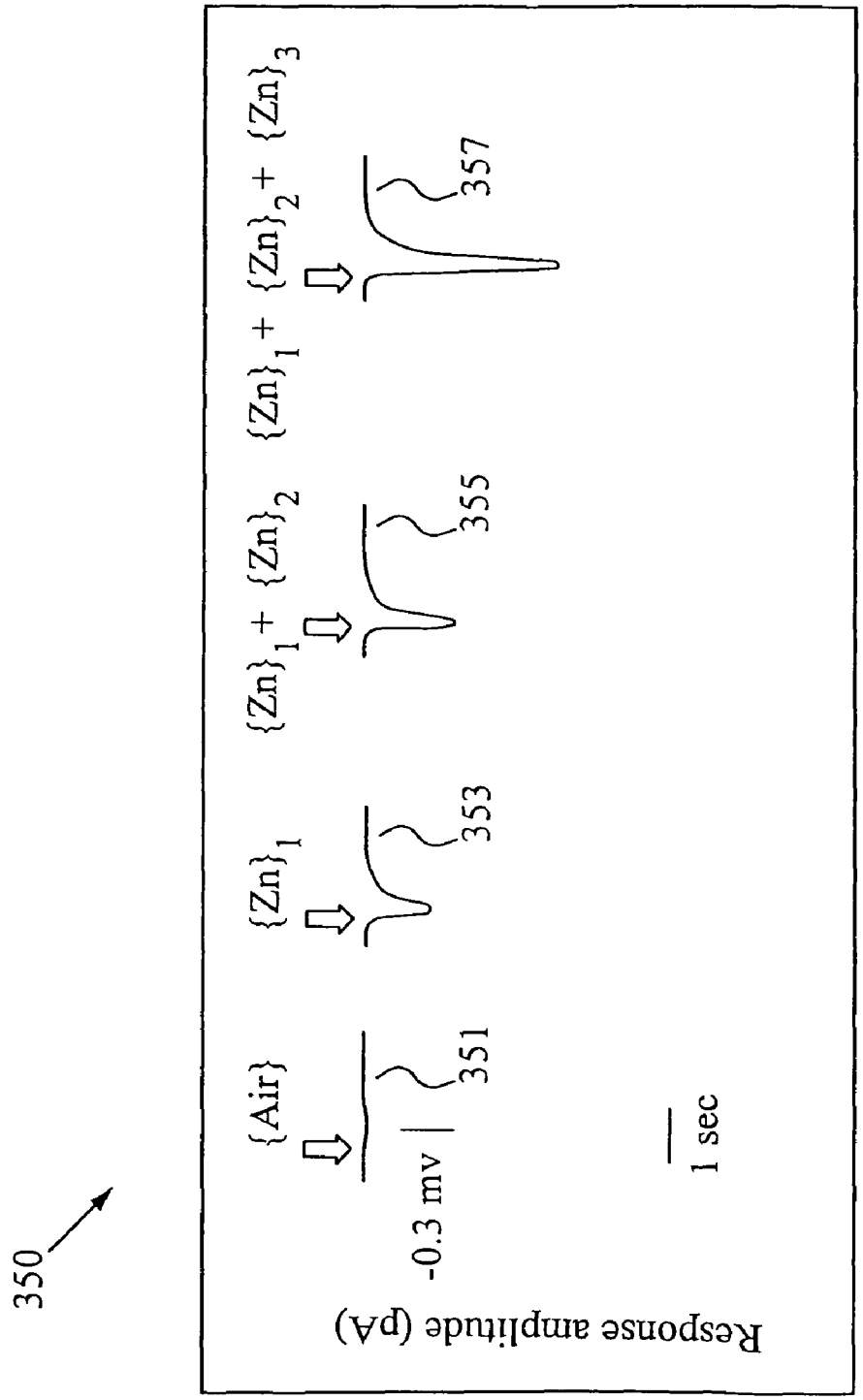
FIG. 3B is a graph of Electroolfactogram recordings of an olfactory tissue exposed to a composition with zinc nanoparticles and an odorant, in accordance with the embodiments of the invention.

FIG. 3B is a graph 350 of amplitude plots 351, 353, 355 and 357 from Electroolfactogram recordings. In this case, an olfactory tissue was treated with a metal composition having zinc nanoparticles and an odorant in an aqueous delivery medium. Each sequential amplitude plot 351, 353, 355 and 357 represents an electrical response as the olfactory tissue is exposed to the metal composition having increased concentrations of zinc nanoparticles. From the amplitude plots 351, 353, 355 and 357, it can be seen that the electrical responses detected greatly increase as the concentration of zinc nanoparticles in the metal composition also increases.

Figure 3C:
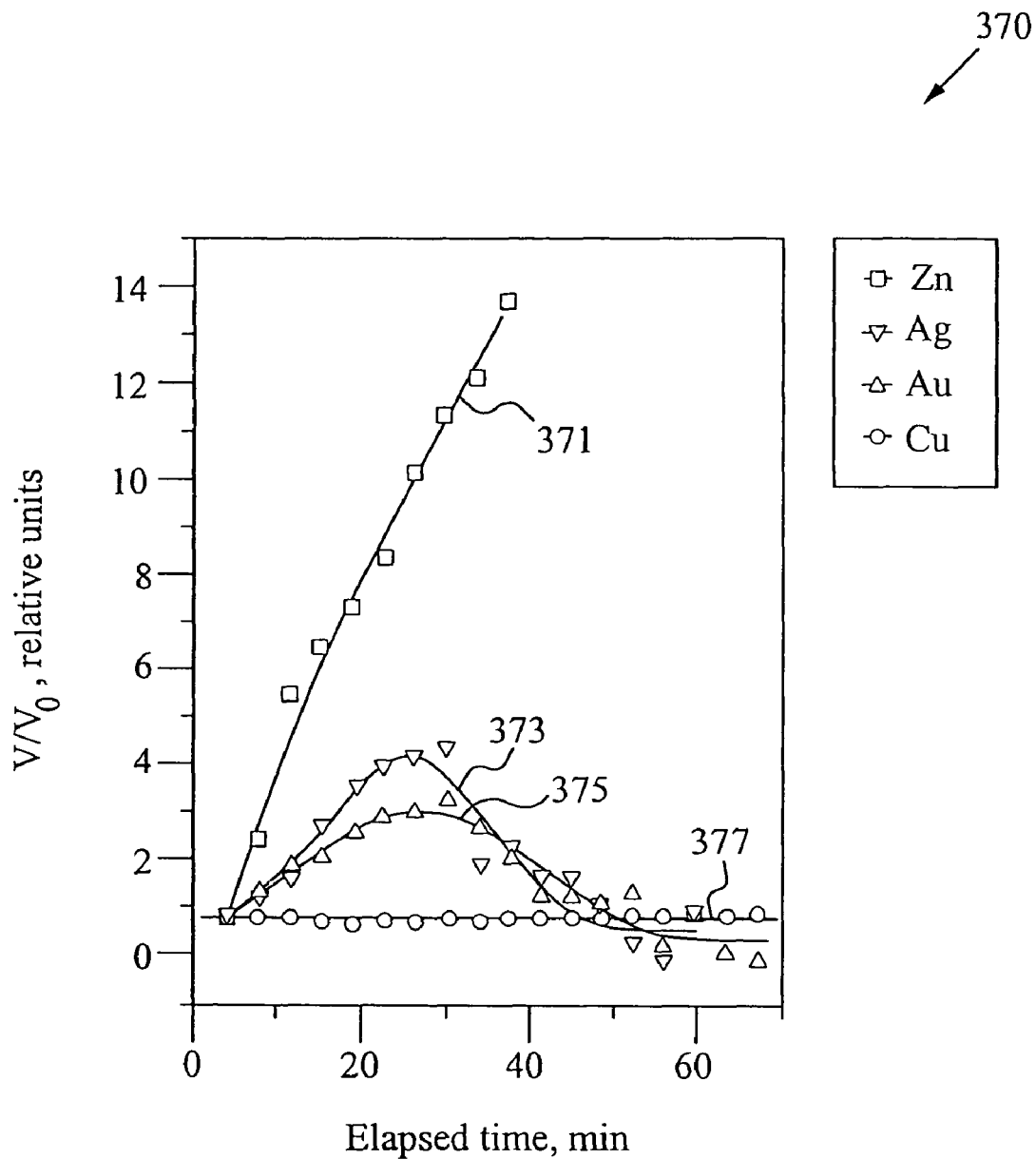
FIG. 3C is a graph of Electroolfactogram recordings of an olfactory tissue exposed to different metal composition and an odorant, in accordance with the embodiments of the invention.

FIG. 3C is a graph 370 showing amplitude plots 371, 373, 375 and 377 of Electroolfactogram recordings. In this case rat olfactory tissue was placed in an EOG recording chamber with a buffer solution and connected to electrodes through an amplifier. Air puffs or plumes of an odorant mixture are applied over the rat olfactory tissue and the electrical response was measured and the normalized peak amplitudes were plotted over time over time. Line 371 indicates that the electrical response to odorant for rat olfactory tissue was most greatly effected by treating the rat olfactory tissue with a composition including zinc nanoparticles.

Figure 4:
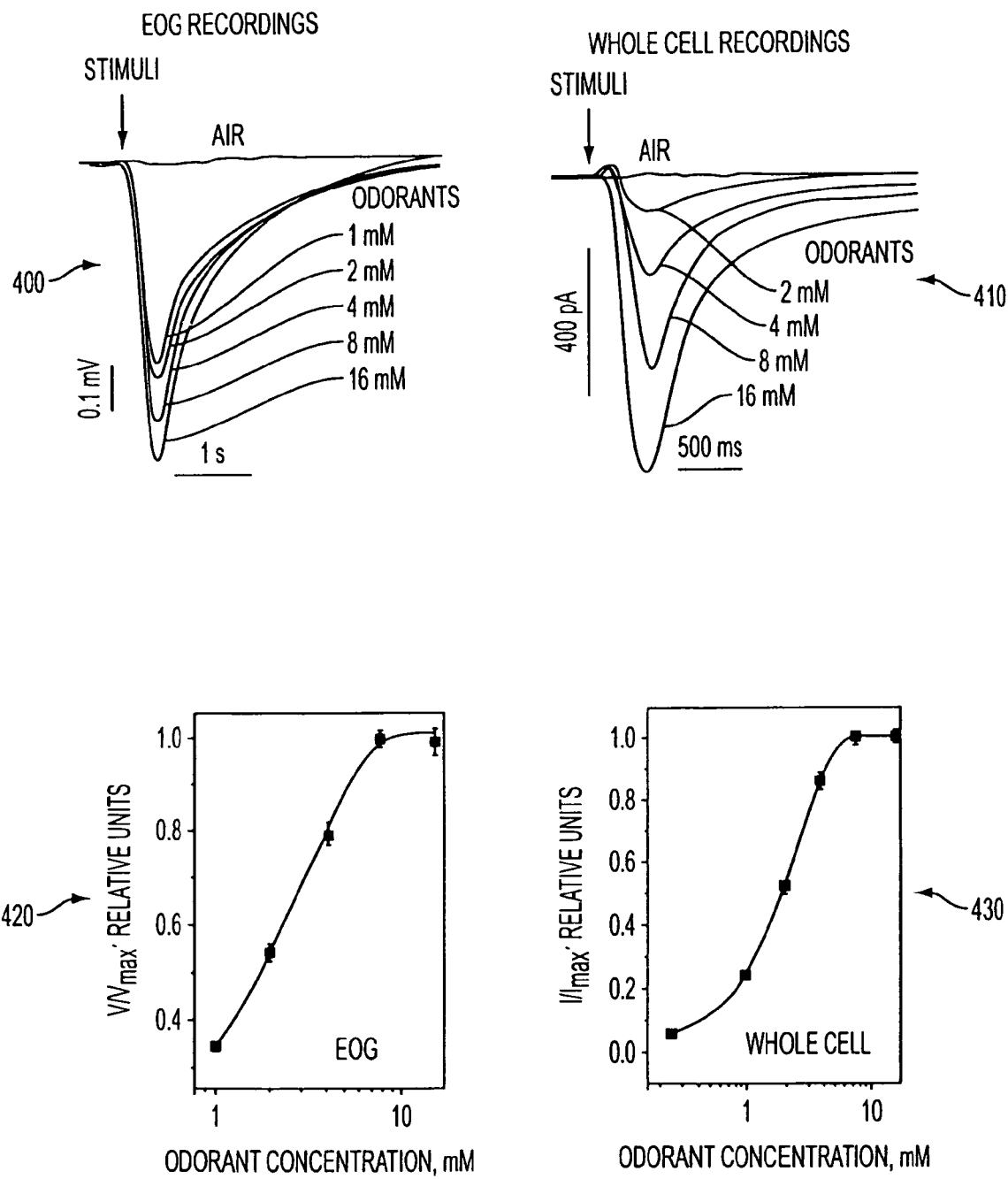
FIG. 4 illustrates several graphs and plots of electrophysiological recordings from a rat epithelium and a single olfactory neuron.

FIG. 4 illustrates several graphs and plots of electrophysiological recordings from a rat epithelium and a single olfactory neuron. Graph 400 shows EOG recordings where the stimulus was a 0.5-s pulse of air or an odorant mixture. The EOG traces were induced by pure air and the odorant mixture at different concentrations. Vapor of odorants were collected above the odorant solutions (in water) of concentrations shown. The higher the concentration of odorant (e.g. 16 mM versus 1 mM), the deeper the voltage spike. Graph 410 shows current traces from whole-cell voltage recordings of olfactory neurons with holding potentials indicating inward current. Again, the higher concentration of odorant results in a deeper current spike. Plot 420 shows a normalized, peak EOG voltage ($V_{peak}/V_{max}$) evoked by the odorant versus odorant concentration. Plot 430 shows a normalized, peak negative current ($I_{peak}/I_{max}$) evoked by odorant versus odorant concentration.

Figure 5:
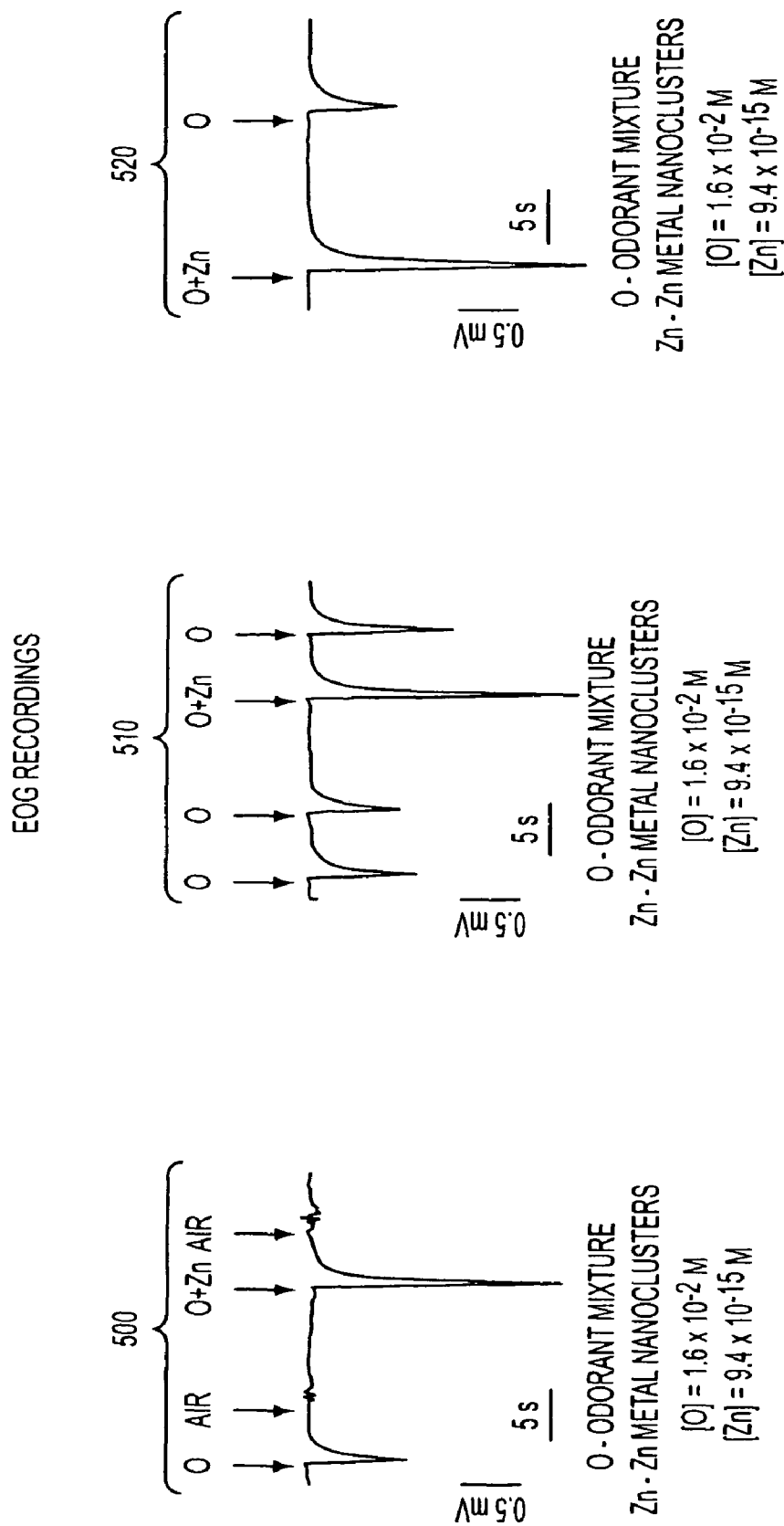
FIG. 5 illustrates EOG traces from rat olfactory epithelium.

FIG. 5 illustrates EOG traces from rat olfactory epithelium. Responses were induced by air odorants and a mixture of odorants and zinc metal particles. In the trace 500, an initial EOG response was induced by an odorant puff (0). Then, after 5 seconds, an air puff (Air) was delivered which evoked only a small disturbance. After 10 more seconds, a mixture of the odorant and a small concentration of zinc metal particles (O+Zn) induced a response that was three times larger than the one induced by the odorant alone. An air puff delivered after the last signal declined did not produce anything but a small disturbance. In the trace 510, two consecutive puffs of odoroant (0) generated normal responses. Then, the odorant plus zinc mixture (O+Zn) generated an enhanced response. After 5 seconds, the odorant alone was delivered and the amplitude of the response was about 40% larger than that evoked by the odorant alone (indicating not all Zn particles were cleared from the receptors). In the trace 520, after the magnified response was induced by the odorant/zinc mixture, the odorant alone generated a normal response (after ~10 seconds), indicating that the receptors were clear of zinc particles delivered by the previous puff. Thus, some time between 5 and 10 seconds is required for the zinc particles to clear. Another conclusion is that the odorant/zinc mixture's effects last less than 10 seconds.

Figure 6:
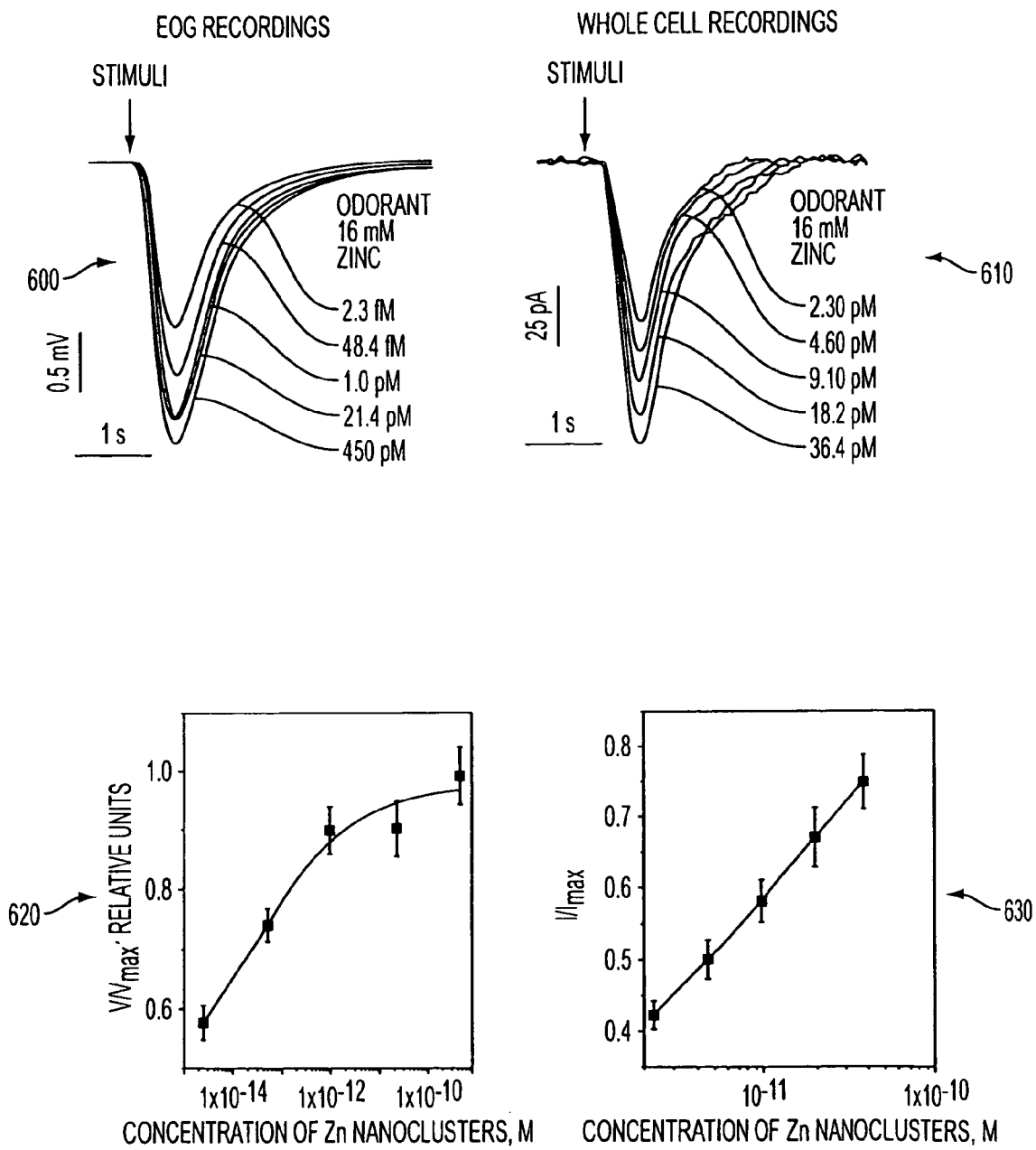
FIG. 6 illustrates electrophysiological recordings from a rat olfactory epithelium and a single olfactory neuron where the stimulus was a 0.5-s pulse of air or an odorant mixture.

FIG. 6 illustrates electrophysiological recordings from a rat olfactory epithelium and a single olfactory neuron where the stimulus was a 0.5-s pulse of air or an odorant mixture. The odorant concentration was constant for all traces. Graph 600 shows EOG traces induced by an odorant/zinc particles mixture at different concentrations of zinc. Vapor of odorants were collected above the odorant solutions (in water) of concentrations shown. The higher the concentration of zinc (e.g. 2.3 fM versus 450 pM), the deeper the voltage spike. Graph 610 shows current traces from whole-cell voltage recordings of olfactory neurons with holding potentials of −70 mV. The stimulus was a 0.5 second pulse of odorant/zinc particle mixture. Downward direction indicates inward current. Again, the higher concentration of zinc results in a deeper current spike. Plot 620 shows a normalized, peak EOG voltage ($V_{peak}/V_{max}$) evoked by the odorant/zinc particles versus zinc concentration. Plot 630 shows a normalized, peak negative current ($I_{peak}/I_{max}$) evoked by odorant/zinc particles versus zinc concentration.

Figure 7:
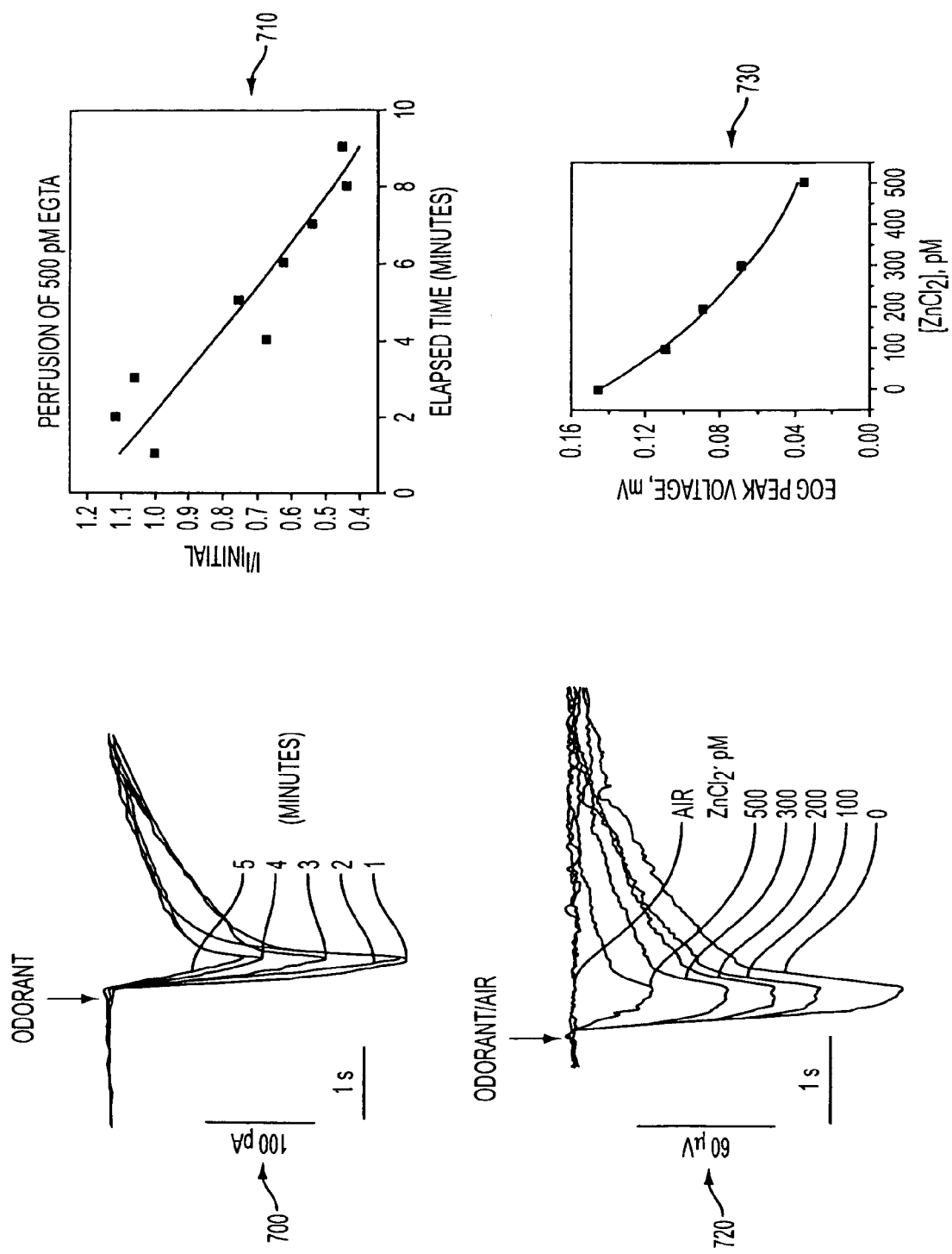
FIG. 7 illustrates results from EGTA experiments and $Zn^{+2}$ ions experiments.

FIG. 7 illustrates results from EGTA experiments and $Zn^{+2}$ ions experiments. 500 pM ethylene glycol tetraacetic acid (EGTA) perfused inside olfactory neurons clearly inhibit odorant response measured by patch-clamp experiments. The effect is dose dependent. It is widely known that EGTA binds multivalent metals. When Zn metal nanoparticles are bound by EGTA, the number of particles participating in olfactory signal transduction is reduced, and the odorant response is decreased. Graph 700 shows results of the whole cell experiments with olfactory receptor neurons. When the patch electrode is filled with a solution containing 500 pM EGTA, the odorant-evoked current changes markedly. Few minutes after beginning the perfusion, a progressive increase in the amplitude of the odorant triggered inward currents is noted. Plot 710 shows change of relative value of peak currents as a result of perfusion by EGTA.

Chart 720 shows EOG traces of rat olfactory epithelium to odorant puff under external perfusion of $ZnCl_2$ solutions. As described, zinc metal nanoparticles enhance odorant responses of olfactory receptor neurons at concentrations of $10^{-9}$-$10^{-15}$ M. Nanoparticles are bound to G-protein in the olfactory signal transduction cascade and provide signal transfer from olfactory receptor to G-protein. When zinc nanoparticles are replaced by $Zn^{+2}$ ions at the same range of concentrations, odorant response by olfactory receptor neurons is reduced, as shown in the chart 720. Plot 730 shows the dependence of peak olfactory response on $ZnCl_2$ concentration and change of relative value of peak currents as a result of perfusion by $Zn^{+2}$ ions. This is due to the inability of $Zn^{+2}$ ions to participate in the signal transduction.

The Zn metal nanoparticles are able to strongly enhance a canine's responsiveness to an odorant. One to two nm metallic nanoclusters contain 40 to 300 atoms of zinc. Adding a small amount of these particles to an odorant is able to increase the sensation of the odorant by a factor of ten. At these concentrations, effects are dose-dependent and reversible. The particles are not toxic and are spontaneously cleared from the system; providing a specific, sensitive, safe and non-invasive technology. An aerosol containing the zinc nanoparticles is able to be sprayed on surfaces (ground, containers, fabrics/clothes, luggage, a person and so on) and dramatically enhance the perception of smell and the ability to detect explosives, drugs and other odors of interest.

It is believed that the compositions and methods described above have a number of applications in controlling the ability of a person to detect one or more odorants. Most notably, the compositions and methods of the present invention are able to be used to increase or enhance a person's ability to detect the one or more odorants.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

What is claimed is:

1. A method of increasing olfactory response to an odorant emanating from an odoriferous surface, the method comprising:
   providing a suspension comprising a solid dispersed phase of zinc metal nanoparticles consisting of from 40 to 300 atoms of metallic zinc per nanoparticle;
   applying the suspension to the odoriferous surface; and
   sniffing the odoriferous surface, thereby nasally inhaling the odorant and the zinc metal nanoparticles, wherein the zinc metal nanoparticles react with olfactory receptors in the nose to increase olfactory response to the odorant.

2. The method of claim 1, wherein the solid dispersed phase yields a concentration of from $2.3 \times 10^{-15}$ to $4.5 \times 10^{-9}$ moles of nanoparticulate zinc metal per liter of suspension.

3. The method of claim 1, wherein the increase in olfactory response lasts less than 10 seconds.

4. The method of claim 1, wherein the suspension is applied to the odoriferous surface in the form of a spray.

5. The method of claim 1, wherein the increase in olfactory response mediated by the zinc metal nanoparticles is dose-dependent.

6. The method of claim 1, wherein the increase in olfactory response mediated by the zinc metal nanoparticles is reversible.

7. The method of claim 1, wherein the suspension is non-toxic.

8. The method of claim 1, wherein the zinc metal nanoparticles are spontaneously cleared from a user's system.

9. A method of increasing olfactory response to an odorant, the method comprising:
   providing a suspension comprising a solid dispersed phase of zinc metal nanoparticles consisting of from 40 to 300 atoms of metallic zinc per nanoparticle;
   applying the suspension to a surface that is proximate an odorant; and
   sniffing the surface, thereby nasally inhaling the odorant and the zinc metal nanoparticles, wherein the zinc metal nanoparticles react with olfactory receptors in the nose to increase olfactory response to the odorant.

10. The method of claim 9, wherein the solid dispersed phase yields a concentration of from $2.3 \times 10^{-15}$ to $4.5 \times 10^{-9}$ moles of nanoparticulate zinc metal per liter of suspension.

11. The method of claim 9, wherein the suspension is applied to the surface in the form of a spray.

12. The method of claim 9, wherein the surface is a surface of an object selected from the group consisting of luggage, container, and clothing.

13. The method of claim 9, wherein the surface is the ground.

14. The method of claim 9, wherein the odorant emanated from an explosive substance.

15. The method of claim 9, wherein the odorant emanated from a drug.

16. A method of increasing olfactory response to an odorant, the method comprising:
   providing a suspension comprising a solid dispersed phase of zinc metal nanoparticles having a particle size in the range of from 1 to 2 nanometers;
   applying the suspension to a surface proximate an odorant; and
   sniffing the surface, thereby inhaling the odorant and the zinc metal nanoparticles through the nose, wherein the zinc metal nanoparticles react with olfactory receptors in the nose to increase olfactory response to the odorant.

17. The method of claim 16, wherein the solid dispersed phase yields a concentration of from $2.3 \times 10^{-15}$ to $4.5 \times 10^{-9}$ moles of nanoparticulate zinc metal per liter of suspension.

18. The method of claim 16, wherein the suspension is applied to the surface in the form of a spray.

19. The method of claim 16, wherein the surface is a surface of an object selected from the group consisting of luggage, container, and clothing.

20. The method of claim 16, wherein the surface is the ground.

21. The method of claim 16, wherein the odorant emanated from an explosive substance.

22. The method of claim 16, wherein the odorant emanated from a drug.

* * * * *